United States Patent [19]

Hani et al.

[11] Patent Number: 5,468,864

[45] Date of Patent: Nov. 21, 1995

[54] PROCESS FOR PREPARING 2,6-DICHLOROPYRIDINE

[75] Inventors: Rahim Hani, Cheshire; Richard H. Dumas, East Haven; David F. Gavin, Cheshire, all of Conn.; Charles H. Harrison; Michael A. Kennedy, both of Rochester, N.Y.; Henry W. Schiessl, Northford, Conn.; Robert E. McMahon, Elizabethtown, Ky.; Steven A. Manke, Wallingford, Conn.

[73] Assignee: Olin Corporation, Cheshire, Conn.

[21] Appl. No.: 190,956

[22] Filed: Feb. 3, 1994

[51] Int. Cl.[6] ................................. C07D 213/61
[52] U.S. Cl. ................................................. 546/345
[58] Field of Search ................................. 546/345

[56] References Cited

U.S. PATENT DOCUMENTS

| | | | |
|---|---|---|---|
| 3,186,994 | 6/1965 | Johnston et al. | 546/345 |
| 3,251,848 | 5/1966 | Taplin, III | 546/345 |
| 3,557,124 | 1/1971 | Stringham et al. | 546/345 |
| 4,054,499 | 10/1977 | Kawamura | 546/345 |
| 4,701,532 | 10/1987 | Humphreys et al. | 546/345 |
| 4,891,108 | 1/1990 | Kilpatrick | 546/345 |
| 5,112,982 | 5/1992 | Kamei | 546/345 |

FOREIGN PATENT DOCUMENTS

| | | |
|---|---|---|
| 2036172 | 2/1990 | Japan . |
| 2036173 | 2/1990 | Japan . |

OTHER PUBLICATIONS

Chemical Abstracts 113:6172, 1990.
Chemical Abstracts 113:6173, 1990.
WPIDS 89–132582, 1989 of JP 01 075469 published Mar. 22, 1989.

Primary Examiner—C. Warren Ivy
Assistant Examiner—D. Margaret M. Mach
Attorney, Agent, or Firm—Dale L. Carlson

[57] ABSTRACT

The present invention relates to a process for preparing 2,6-dichloropyridine which comprises reacting an organic solvent-free, catalyst-free reaction mixture comprising 2-chloropyridine and chlorine in the presence of a hydrogen chloride scavenger and ultraviolet light, and optionally in the presence of added moisture, at a temperature of between about 90° C. and about 185° C. Also claimed is a method for preventing calcium chloride plugging of the chlorine feed stream and for preventing calcium chloride build-up in the above reaction mixture which comprises adding moisture in the form of water or steam, or a combination thereof, to the reaction mixture prior to, or during, the reaction of said process.

11 Claims, No Drawings

PROCESS FOR PREPARING 2,6-DICHLOROPYRIDINE

FIELD OF THE INVENTION

The present invention relates generally to a process for preparing 2,6-dichloropyridine and, more specifically, to a process comprising chlorination of 2-chloropyridine in the presence of UV light and an acid scavenger, and optionally in the presence of added water, in the absence of a solvent and in the absence of a catalyst.

BACKGROUND OF THE INVENTION

Polychloropyridines are well-known to be useful intermediates in the preparation of agricultural chemicals, pharmaceuticals and antimicrobial compounds. 2,6-dichloropyridine is one such intermediate, and there are several known processes for making this intermediate from 2-chloropyridine. In recent years, there has been a trend in the industry away from the use of catalysts in preparing the 2,6-dichloropyridine since catalysts typically require additional expense, as well as processing costs associated with catalyst removal from the desired product. Illustrative of this trend, U.S. Pat. No. 5,112,982 discloses a process for preparing 2,6-dichloropyridine by reacting 2-chloropyridine with chlorine in a liquid phase at a temperature not lower than 160° C. in the absence of a catalyst. Unfortunately, the reaction of the process of the '982 patent takes longer than might otherwise be desired, as shown by the working examples of the '982 patent which involve reaction times ranging between 40 hours (Example 2 of the patent) and 50 hours (Example 1 of the patent).

Other processes which typically do not require the use of catalysts are also known. By way of illustration, U.S. Pat. No. 3,557,124 discloses a process for the production of 2,6-dichloropyridine in a liquid phase reaction at a temperature within a range of from 90° C. to 180° C. Unfortunately, the product yields obtained using the process of the '124 patent are sometimes lower than might be desired, as shown in the first run of Example 1 (72.3 percent yield) and in Example 4 (76 percent yield) of this patent.

As still another illustration, U.S. Pat. No. 3,251,848 discloses a vapor phase process for producing 2,6-dichloropyridine which comprises rapidly mixing, in a turbulent flow system and a preferred temperature range of from about 370° C. to about 395° C. Unfortunately, this preferred temperature range is considerably higher than might be desired from a processing cost standpoint.

Illustrative of other processes for preparing polychloropyridines are the following: U.S. Pat. No. 3,186,994 discloses a process employing polychloro-(trichloromethyl) pyridine as a starting material; and, U.S. Pat. No. 4,701,532 discloses the selective chlorination of 2-chloro-5-(trichloromethyl) pyridine in a liquid phase reaction using an effective amount of $Cl_2$ at an elevated pressure and elevated temperature in the range of 60° to 180° C. in the absence of an added catalyst. However, these processes generally produce product mixtures, and the selectivity to, and purity of, the desired specific product typically is lower than might be wanted.

Another noteworthy trend in recent years has been away from the use of environmentally unfriendly solvents, such as carbon tetrachloride. However, heretofore, organic solvent-free processes have generally required higher temperatures than might be desired.

New processes for producing 2,6-dichloropyridine that are simple, do not employ a catalyst and do not employ an organic solvent, and yet provide good selectivity to a highly pure desired product without significant amounts of byproduct production, would be desired by the 2,6-dichloropyridine manufacturing community. The present invention provides one such process.

SUMMARY OF THE INVENTION

In one aspect, the present invention relates to a process for preparing 2,6-dichloropyridine, which comprises reacting an organic solvent-free, catalyst-free reaction mixture comprising (and advantageously consisting essentially of) 2-chloropyridine and chlorine in the presence of a hydrogen chloride scavenger and ultraviolet light, and optionally in the presence of added water, at a temperature of between about 90° C. and about 185° C.

In another aspect, the present invention relates to a process for preparing 2,6-dichloropyridine which comprises reacting a reaction mixture comprising 2-chloropyridine and chlorine, in the presence of calcium carbonate as a hydrogen chloride scavenger, and in the presence of liquid water or steam or a combination thereof at a reaction temperature in the range of between about 90° C. and about 125° C.

These and other aspects will become apparent upon reading the following detailed description of the invention.

DETAILED DESCRIPTION OF THE INVENTION

It has now been surprisingly found in accordance with the present invention that the use of a hydrogen chloride scavenger in the above-described reaction mixture effectively prevents the formation of unwanted hydrochloride salts of chloropyridine or dichloropyridine that tend to either clog the reactor outlet or cause formation of unwanted chloropyridine isomers, such as 2,5-dichloropyridine. The use of the hydrogen chloride scavenger facilitates good selectivity to the desired 2,6-dichloropyridine product. In addition, it has now been found that the use of water (preferably in the form of steam, liquid water or a combination of water and steam), together with the hydrogen chloride scavenger, facilitates the production of the desired 2,6-dichloropyridine at a relatively low temperature and/or a moderated rate of reaction, thereby avoiding charring of the product. Likewise, the use of added water tends to minimize formation of solid calcium chloride by-product which can cause plugging of the chlorine feed stream and coating of the light source.

Although the reaction temperature employed is suitably in the range of between about 90° C. and about 185° C., the preferred reaction temperature is between about 150° C. and about 185° C. when the reaction is conducted in the absence of added moisture, and is preferably between about 90° C. and about 125° C. when the reaction is conducted in the presence of added moisture. The reaction is suitably conducted at atmospheric or superatmospheric pressure, most preferably at a pressure at or near reflux temperature. Preferably, the hydrogen chloride scavenger is selected from the group consisting of organic and inorganic bases, more preferably selected from the group consisting of amines, oxides, hydroxides, carbonates and bicarbonates. A particularly preferred hydrogen chloride scavenger is calcium carbonate.

The chloropyridine reactant useful in the process of the present invention may be 2-chloropyridine alone, or a mixture of 2-chloropyridine and 2,6-dichloropyridine. The 2,6- dichloropyridine present in the starting material does not undergo further reaction under the above-specified conditions of the process of the present invention.

Since the rate of chlorine conversion in the reaction system varies depending on the form or shape of a reaction vessel to be employed, the rate at which chlorine is to be charged is appropriately determined by measuring chlorine concentration in the exhaust gas. As a general rule, the rate of chlorine conversion increases with an increase of temperature or pressure or an increase of 2-chloropyridine reactant concentration. Preferably, the chlorine is employed in gaseous form in the reaction mixture in at least an equimolar amount relative to the amount of the 2-chloropyridine reactant.

The hydrogen chloride scavenger is suitably employed in an amount of between about 0.10 and about 2 (preferably between about 0.5 and about 2) molar equivalents, based upon the molar amount of the 2-chloropyridine reactant employed. Most preferably, at least a stoichiometric amount of the hydrogen chloride scavenger is employed relative to the amount of HCl evolved.

The amount of added water (liquid water, steam, or a combination thereof), if used, can vary over a wide range. Preferably, sufficient water is present to dissolve all of the $CaCl_2$ formed during the reaction in order to enjoy the full advantage of water addition, i.e. avoiding encrustations of solids on the light surfaces, reactor walls and $Cl_2$ inlet. In this regard, the amount of calcium chloride formed depends on the depth of chlorination reaction, i.e. how far the chlorination reaction is allowed to proceed. The maximum amount of water employed is a function of the desired reactor productivity, i.e. too much water reduces the amount of product that can be produced per hour per gallon of reactor volume. Generally, the water (if used) is added in an amount of between about 10 and about 75 (preferably between about 10 and about 50) weight percent based upon the amount of the 2-chloropyridine reactant employed.

In the process of this invention, a reaction solvent (other than added moisture) is not used, and this is believed to provide a significant advantage from an environmental standpoint relative to the many prior art processes that employ an organic solvent.

The following examples are intended to illustrate, but in no way limit the scope of the present invention.

COMPARATIVE EXAMPLE A

Chlorination of 2-chloropyridine in the Absence of a Hydrogen Chloride Scavenger 562.8 grams (g.) of 2-chloropyridine (2-CP) was charged to a 500 ml photochemical apparatus equipped with a quartz lamp well and a 12 watt low pressure UV lamp and heated to 163° C. Chlorine was introduced via a dip tube at 61 L/hr for two hours. The reaction temperature during the run was 150° C. Solid 2-chloropyridine hydrochloride formed which eventually blocked the reactor outlet, causing a pressure build-up and terminating the run. 576.3 g of reaction mixture was recovered. G.C. analysis of the reaction mixture found 88.5% 2-CP, 7.9% 2,6-dichloropyridine (2,6-DCP), 0.96% dichloropyridine, 0.87% trichloropyridine, 1.19% tetrachloropyridine, 0.02% pentachloropyridine and 0.49% dipyridyls. The selectivity (moles 2,6-DCP produced/mole 2-CP consumed) was 69.2% and the yield (moles 2,6-DCP produced/mole 2-CP charged) was 6.2%.

EXAMPLE 1

Chlorination of 2-chloropyridine in the Presence of a Calcium Carbonate Scavenger for Hydrogen Chloride 340.5 grams (g.) 2-chloropyridine (2-CP) and 60.1 g $CaCO_3$ were charged to a 500 ml photochemical apparatus equipped with a quartz lamp well and a 12 watt low pressure UV lamp and heated to 165° C. Chlorine was introduced via a dip tube at 65 L/hr for two hours. The temperature during the reaction was 150° C. No 2-chloropyridine hydrochloride formed in the reactor outlet. 353.3 g of reaction mixture was recovered. G.C. analysis of the reaction mixture found 69.3% 2-CP, 29.4% 2,6-dichloropyridine (2,6-DCP), 0.75% other dichloropyridine, 0.22% trichloropyridine, 0.1 tetrachloropyridine, 0.01% pentachloropyridine and 0.27 dipyridyls. The selectivity (moles 2,6-DCP produced/mole 2-CP consumed) was 84.8% and the yield (moles 2,6-DCP produced/mole 2-CP charged) was 23.5%.

COMPARATIVE EXAMPLE B

Chlorination of 2-chloropyridine in the Absence of a Hydrogen Chloride Scavenger 345.9 g 2-chloropyridine (0.86% $H_2O$, 99.3% 2-CP dry basis, 3 moles) was charged to a mechanically stirred 4-neck flask with gas inlet tube and reflux condenser. The reactor was heated to reflux (134° C.) and illuminated with a 100 W Spectroline® lamp with its UV filter removed. Chlorine gas (3 moles) was bubbled in at 34 L/hr for 2 hrs. The reaction temperature rose to 149° C. by the end of the chlorine addition. After 30 minutes a heat gun had to be used to melt 2-chloropyridine hydrochloride that formed in the condenser. At the end of the chlorine addition the heat and chlorine were shut off. Nitrogen was bubbled in as the reactor cooled to room temperature. 100 ml of water was added and the pH of the mixture was adjusted to 7.5 with 17.4 g 50% NaOH. The mixture was phased and 377.7 g of organics were recovered. A GC analysis of this material found 63.8% 2-chloropyridine and 32.0% 2,6-dichloropyridine. The conversion (moles 2-chloropyridine consumed/mole 2-chloropyridine fed) was 29.2%. The selectivity (moles 2,6-dichloropyridine produced/mole 2-chloropyridine converted) was 93.1%. The product was dark brown in color.

EXAMPLE 2

Chlorination of 2-chloropyridine in the Presence of a Calcium Carbonate Scavenger for Hydrogen Chloride 345.9 g 2-chloropyridine (0.86% $H_2O$, 99.3% 2-CP dry basis, 3 moles), and 75.07 g $CaCO_3$ were charged to a mechanically stirred 4-neck flask with gas inlet tube and reflux condenser. The reactor was heated to reflux (124° C.) and illuminated with a 100 W Spectroline lamp with its UV filter removed. Chlorine gas (3 moles) was bubbled in at 34 L/hr for 2 hrs. The reaction temperature rose to 146° C. by the end of the chlorine addition. The reaction mixture was filtered and the solid portion was washed with methylene chloride. The methylene chloride solubles were combined with the rest of the organics and stripped to remove the solvent, leaving 366.2 g. The organics were analyzed by GC and found to contain 62.4% 2-chloropyridine and 34.8% 2,6-dichloropyridine. The conversion was 32.9% and the selectivity was 87.2%. The product was light yellow in color.

EXAMPLE 3

Chlorination of 2-chloropyridine in the Presence of a Calcium Carbonate Scavenger for Hydrogen Chloride without Added Water This trial is typical of a non-aqueous chlorination of 2-chloropyridine with no water added except that adventitiously introduced with the starting material and that formed in the reaction of the co-product HCl and the calcium carbonate base. Enough base was added to convert half the starting chloropyridine to 2,6-dichloropyridine.

340 g 2-chloropyridine (99.5% assay, 2.98 moles) was charged to a 500 ml, 4-neck, round-bottom Pyrex flask provided with a heating mantle, thermometer and reflux condenser connected to a caustic scrubber to trap excess chlorine and HCl. Chlorine gas was introduced through a fritted sparge tube. A mechanical stirrer provided agitation for the reaction mass.

74.9 g (0.75 mole) calcium carbonate (50% of theory) was added, the reaction slurry heated to ca. 160° C. and chlorine addition begun at ca. 15 L/hr. The UV light was then turned on and directed from outside the flask to illuminate the vapor phase. The U.V. light used was a Spectroline® Model B-100 y (115 volt, 3.3 amp) lamp with a 100 W medium pressure Hg U.V. light. The reaction was carried out for three hours with the temperature maintained at 150° C. Upon completion of the reaction, the reactor walls were encrusted with solids. Gas chromatographic analysis of the reaction mixture showed (wt. %):

| | |
|---|---|
| 2-chloropyridine | 49.2 |
| 2,6-dichloropyridine | 42.5 |
| Other chlorinated species | 0.9 |
| High-boilers, not otherwise identified | 7.4 |

EXAMPLE 4

Chlorination of 2-chloropyridine in the Presence of a Calcium Carbonate Scavenger for Hydrogen Chloride with Added Water Example 3 was repeated, using the same apparatus and U.V. light source, but adding 20% water at the start of the run to achieve the benefits of an aqueous system, already enumerated above.

278 g (2.436 mole) 2-chloropyridine was charged to the reaction flask along with 60.3 g (0.602 mole) calcium carbonate (50% of theory for complete chlorination) and 69.2 g (3.844 mole) water to give a 20% water/2-chloropyridine solution. The reaction was heated to reflux (98° C.), addition of chlorine was begun at ca. 15 L/hr. and the UV light was turned on. The reaction was heated for 3 hours, with the temperature gradually increasing to 120° C. The final reaction mixture consisted of two liquid layers. The reactor was clean and free of encrustations. The upper layer, which solidified upon cooling, was analyzed by gas chromatography. The analysis was (wt. %):

| | |
|---|---|
| 2-chloropyridine | 52.0 |
| 2,6-dichloropyridine | 46.2 |
| Other chlorinated species | 1.1 |
| High-boilers | 0.7 |

The analyses of the products from Example 4 and from Example 3, in which water was not added, shows that in the aqueous system, the selectivity of the reaction to give the desired 2,6-dichloropyridine is 96.5% compared to 81.5% in the absence of added water, and the conversions were 41.4% and 44.8%.

While the invention has been described above with reference to specific embodiments thereof, it is apparent that many changes, modifications and variations can be made without departing from the inventive concept disclosed herein. Accordingly, it is intended to embrace all such changes, modifications and variations that fall within the spirit and broad scope of the appended claims. All patent applications, patents and other publications cited herein are incorporated by reference in their entirety.

What is claimed is:

1. A process for preparing 2,6-dichloropyridine, in a molar selectivity of at least 81.5%, which comprises reacting a catalyst-free reaction mixture that is free of an organic solvent and that consists essentially of 2-chloropyridine and chlorine in the presence of ultraviolet light and a hydrogen chloride scavenger at a reaction temperature of between about 90° C. and about 185° C.

2. The process of claim 1 wherein said reaction mixture contains 2,6-dichloropyridine in admixture with said 2-chloropyridine.

3. The process of claim 1 wherein said hydrogen chloride scavenger is employed in said reaction mixture in an amount of between about 10 molar percent and about 200 molar percent based upon the molar amount of the 2-chloropyridine reactant employed.

4. The process of claim 1 wherein said hydrogen chloride scavenger is employed in an amount of between about 50 molar percent and about 200 molar percent based upon the molar amount of the 2-chloropyridine reactant employed.

5. The process of claim 1 wherein said hydrogen chloride scavenger is an organic or inorganic base.

6. The process of claim 5 wherein said inorganic base is selected from the group consisting of oxide, hydroxide, carbonate and bicarbonate moieties, and combinations.

7. The process of claim 1 wherein said reaction mixture additionally contains added water in the form of liquid water, steam or a combination thereof.

8. A process for preparing 2,6-dichloropyridine which comprises reacting a catalyst-free reaction mixture free of an organic solvent and consisting essentially of 2-chloropyridine and chlorine, in the presence of ultraviolet light, and calcium carbonate as a hydrogen chloride scavenger, and in the presence of water or steam or a combination thereof, at a reaction temperature in the range of between about 90° C. and about 125° C.

9. The process of claim 8 wherein said hydrogen chloride scavenger is employed in said reaction mixture in an amount of between about 0.1 molar equivalent and about 2 molar equivalents based upon the molar amount of the 2-chloropyridine reactant employed.

10. The process of claim 8 wherein said hydrogen chloride scavenger is employed in an amount of between about 0.5 molar equivalent and about 2 molar equivalents based upon the molar amount of the 2-chloropyridine reactant employed.

11. The process of claim 8 wherein said water or steam or combination thereof is employed in a total amount of between about 10 and about 75 weight percent based upon the amount of 2-chloropyridine employed in said reaction mixture.

* * * * *